United States Patent [19]

Colleran

[11] Patent Number: 5,782,920
[45] Date of Patent: Jul. 21, 1998

[54] OFFSET COUPLING FOR JOINT PROSTHESIS

[75] Inventor: Dennis P. Colleran, Plainville, Mass.

[73] Assignee: Johnson & Johnson Professional, Inc., Raynham, Mass.

[21] Appl. No.: 748,999

[22] Filed: Nov. 14, 1996

[51] Int. Cl.⁶ .................................. A61F 2/30; A61F 2/38
[52] U.S. Cl. .................................. 623/18; 623/20; 403/306
[58] Field of Search .................................. 623/16, 17, 18, 623/20, 39; 403/306, 307, 301, 299

[56] References Cited

U.S. PATENT DOCUMENTS

| | | | |
|---|---|---|---|
| 4,538,305 | 9/1985 | Engelbrecht et al. | 623/20 |
| 4,950,297 | 8/1990 | Elloy et al. | 623/20 |
| 4,985,037 | 1/1991 | Petersen | 623/20 |
| 5,133,760 | 7/1992 | Petersen et al. | 623/20 |
| 5,194,066 | 3/1993 | Van Zile | 623/20 |
| 5,226,915 | 7/1993 | Bertin | 623/20 |
| 5,271,737 | 12/1993 | Baldwin et al. | 623/20 |
| 5,290,313 | 3/1994 | Heldreth | 623/20 |
| 5,330,534 | 7/1994 | Herrington et al. | 623/20 |
| 5,545,228 | 8/1996 | Kambin | 623/17 |

*Primary Examiner*—Mary Beth Jones
*Attorney, Agent, or Firm*—Nutter, McClennen & Fish, LLP

[57] ABSTRACT

A joint prosthesis component system allows an inferior component of a prosthesis system to be offset from a superior component of the system. In one embodiment the joint prothesis component system comprises a tibial tray having an offset tibial stem. An adapter element connects between the tibial tray and tibial stem to provide the desired degree of offset and the orientation of the offset. The adapter element is constructed such that a longitudinal axis extending through a first end thereof is offset from a longitudinal axis extending through a second end thereof.

19 Claims, 4 Drawing Sheets

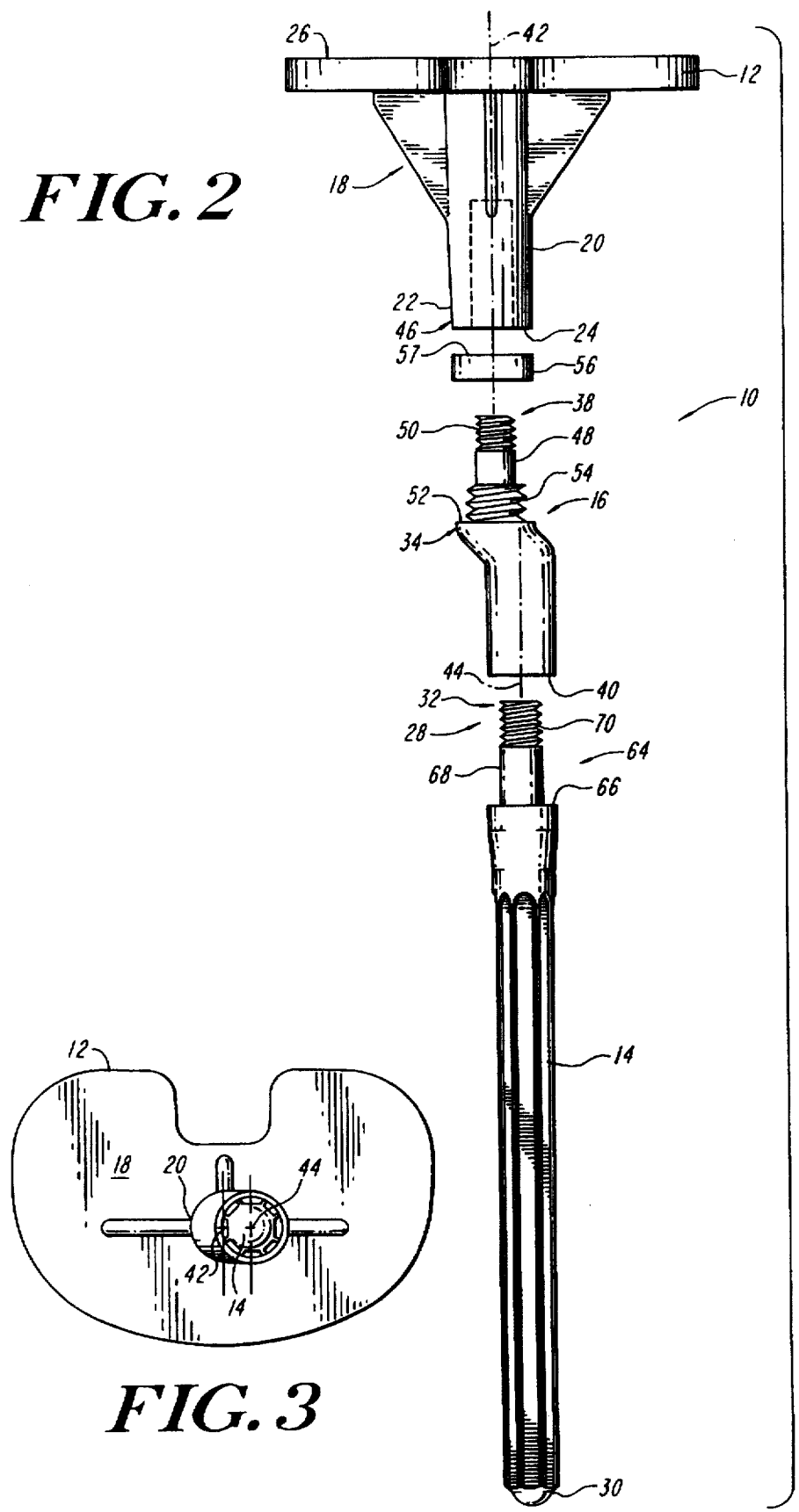

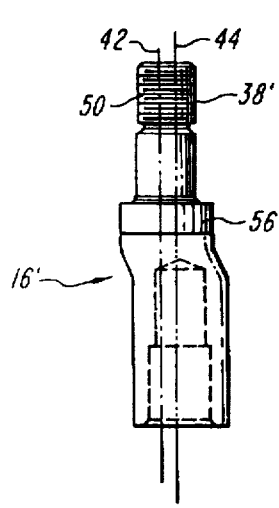 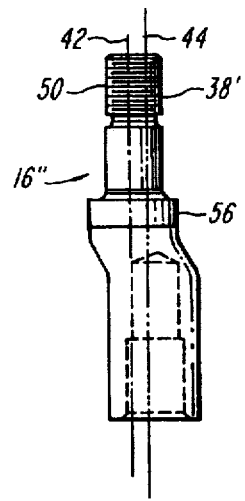 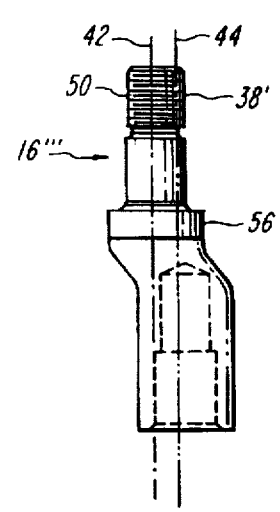
FIG.4A   FIG.4B   FIG.4C
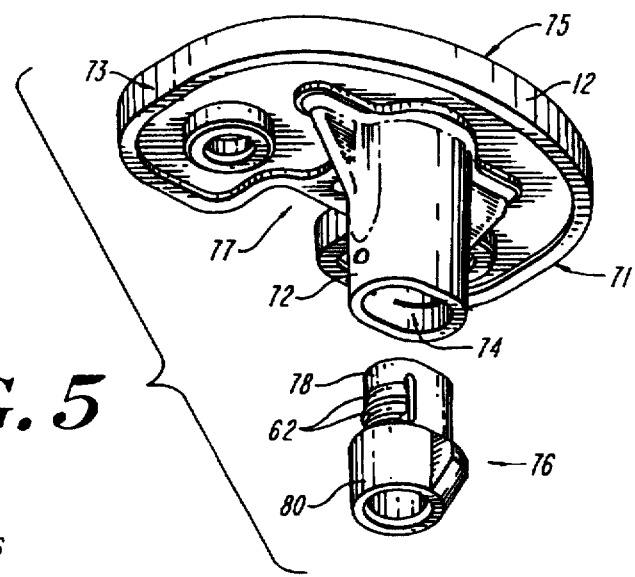
FIG.5
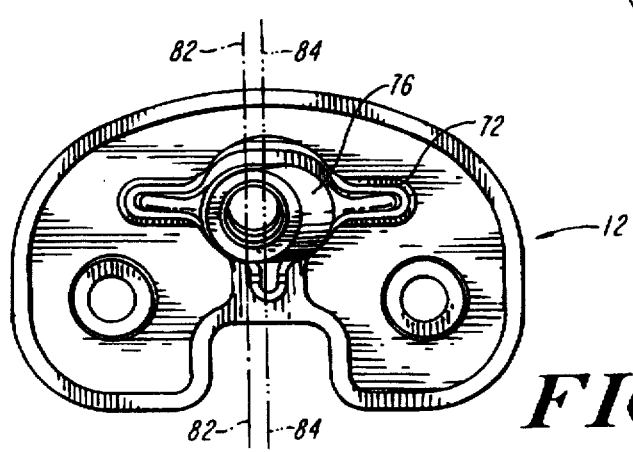
FIG.6

5,782,920

1

OFFSET COUPLING FOR JOINT PROSTHESIS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to modular joint prothesis components in which one end of the prothesis component is laterally offset with respect to the other end thereof. More particularly, the invention relates to knee prostheses components in which the tibial stem is laterally offset with respect to a longitudinal axis of the tibial tray.

Various joint prosthesis components include elongate stems that are to be mounted within the intramedullary canal of a bone while the other end is attached to another prosthesis component that is mounted upon the bone. Such stems are used, for example, with femoral knee stems and tibial knee stems. The large variation in the human anatomy of different patients creates the need for a variety of implant sizes and configurations. In some instances, it is necessary that the longitudinal axis of the stem be laterally offset from the longitudinal axis of the other prosthesis component. Knee arthroplasty procedures, for example, involve the installation of a femoral component on the patient's femur and a tibial component on the patient's tibia. The tibial component usually comprises a tibial stem which is attachable to a tibial tray. The tibial stem is designed to be installed within the intramedullary canal of the tibia while the tibial tray mounts upon a prepared surface on the head of the tibia. A tibial bearing member, which articulates with the femoral component, is typically mounted upon the tibial tray.

The tibia is one example of a bone in the human skeletal system that exhibits great variation among patients. Some knee arthroplasty patients may require that the tibial stem prosthesis component be implanted in an orientation such that the longitudinal axis of the tibial stem be colinear with the longitudinal axis of the tibial tray prosthesis component. In other individuals these axes must be offset with respect to one another to ensure proper implantation of the tibial stem. Even where offset is required, there is no uniformity as to the degree or direction of offset.

Modular prosthesis systems have been developed to accommodate the variability in patient anatomies. Modular systems include a number of interchangeable parts, each having different sizes or other physical characteristics. Such modular systems are useful in that they allow surgeons to use one or more standard parts with interchangeable components having different characteristics.

U.S. Pat. No. 5,290,313 discloses a modular tibial prothesis in which a tibial stem is mounted so as to be laterally offset with respect to the longitudinal axis of a tibial tray. A coupling allows specially designed tibial stems to be mounted to the tibial tray to achieve a desired offset orientation. One disadvantage of this design is that the tibial stems themselves are offset, and a different stem must be used to achieve a desired offset orientation. As a result, a number of different, non-standard tibial stems are needed to achieve the desired offset orientation required for a given patient. Such a system can increase the cost of prostheses because several non-standard parts are necessary to cope with all possible anatomical requirements of patients.

Modular joint prosthesis components are needed which optimize the fit within the patient while, at the same time, allowing greater flexibility to the surgeon. It would also be desirable to be able to achieve optimal fit of prosthesis components while still reducing the inventory of joint prosthesis parts that are needed to meet patient needs.

SUMMARY OF THE INVENTION

The invention provides a modular joint prosthesis in which one component, which is mountable within bone, is able to be offset from another, attached component that is adjacent thereto, and which is mountable upon the bone. Although the invention is applicable to a variety of joint prosthesis components, it is described herein for purposes of exemplification, with respect to a tibial component of a knee prothesis.

A joint prothesis element, such as a tibial tray, has an inferior surface that is mountable upon bone and an opposed superior surface. An elongate member extends from the inferior surface of the tray and has on a distal end thereof a connection surface that is matable with other prothesis components. A stem, such as a tibial stem, is able to be joined to the tray element by way of an adapter element that can enable the stem to achieve a desired offset orientation.

The adapter element includes first and second ends wherein a longitudinal axis extending through the first end is substantially parallel to but offset from a second longitudinal axis extending through the second end of the adapter. The first end of the adapter element has a connection surface that is matable with the connection surface on the distal end of the elongate extension. The second end of the adapter element is matable with the proximal end of the elongated stem.

The adapter element can be affixed to the distal end of the elongate extension of the tibial tray to the stem by a variety of fastening techniques, including threaded connections, interference fit and mechanical engagement. In one embodiment, the first end of the adapter element can be of a non-circular shape, e.g., oval, polygonal or star-shaped, to facilitate orientation of the stem in a variety of positions.

BRIEF DESCRIPTION OF THE DRAWINGS

FIG. 2 is an exploded view of the joint prothesis component of FIG. 1.

FIG. 3 is a bottom view of the joint prothesis component shown in FIG. 1.

FIGS. 4A, 4B and 4C are side views of adapter elements of the type shown in FIGS. 1 and 2, each having a different degree of offset.

FIG. 5 is an exploded, perspective view of another embodiment of a joint prothesis component of the invention, illustrating a tibial tray and an adapter element.

FIG. 6 is a bottom view of the joint prothesis components shown in FIG. 5 in an assembled condition.

DETAILED DESCRIPTION OF THE INVENTION

Figure 1:
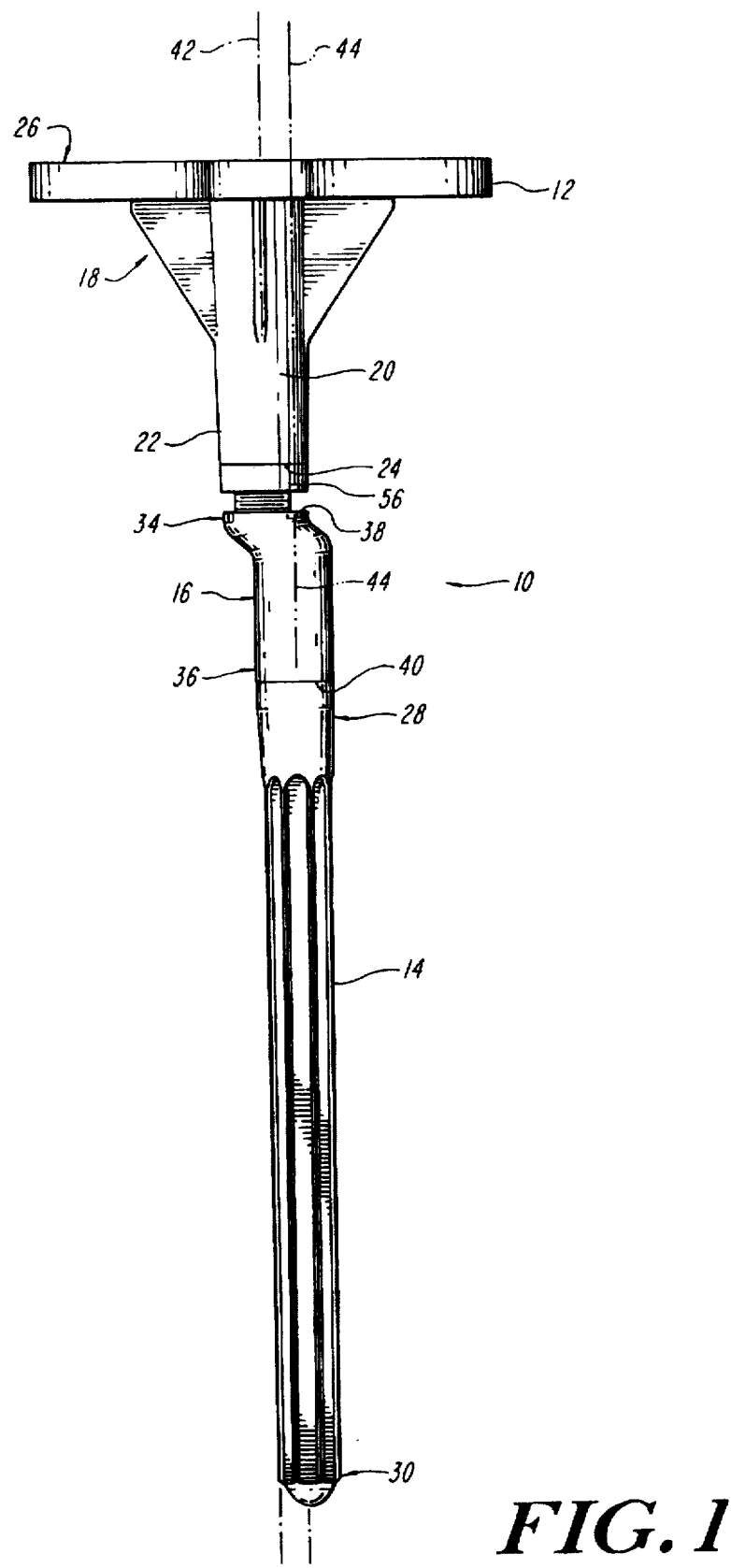
FIG. 1 is a perspective view of a joint prothesis component of the present invention, including a tibial tray and a tibial stem that are joined together in an offset manner by an adapter element.

Referring to FIG. 1, a joint prothesis component system 10 is provided. The component system 10 includes a tray element 12 that is joined to a stem element 14 through a selectively removable and replaceable adapter element 16. In the embodiment illustrated herein, the joint prothesis components are shown as tibial trays and tibial stems useful as components of a knee joint prothesis system. It is understood, however, that the invention applies to components of other prothesis systems in which a longitudinal axis of a first element, that is mountable upon bone, is desired to be offset from the longitudinal axis of a second element that is attachable to the first element and mountable within bone.

With reference to FIGS. 1 through 3, the tray element 12 can be a tibial tray of a type that is known in the art. The tray includes a first, inferior surface 18 that is adapted to mount upon a patient's tibia (not shown). The inferior surface includes an elongate extension 20, preferably integral with the tibial tray, that is intended to mount within the intramedullary canal of the tibia. A distal end 22 of the elongate extension 20 includes a connection surface 24. The tray element 12 also includes a second, superior surface 26 upon which other prothesis components, such as a tibial bearing member (not shown), are mountable.

Adapter element 16 is intended to join the tibial stem 14 to the tray element 12 such that these components are in a desired orientation with respect to one another. The adapter element 16 includes a first, proximal end 34 and a second, distal end 36. The proximal and distal ends 34, 36, each have connection surfaces 38, 40, respectively, which allow the adapter element to mate with the elongate extension 20 of the tray element 12 and the proximal end 28 of the stem element. Further, the proximal end 34 of the adapter element 16 has a longitudinal axis 42 extending therethrough that is offset from the longitudinal axis 44 extending through the distal end 36 of adapter element 16. The degree of offset can vary from 1 to 4 mm as required by patient anatomy. Generally, however, the degree of offset will range from about 1 to 6 mm.

The stem element 14 is an elongate member having a proximal end 28 and a distal end 30. The proximal end 28 of the tibial stem includes a connection surface 32, enabling it to be matable with the connecting surface 40 on the distal end 36 of adapter element 16. Stem element 14, when assembled to the remaining prosthesis components, is intended to be mounted within the intermedulary canal of a patient's tibia in order to firmly secure the tibial component of the knee or the prosthesis to the tibia.

In the embodiment illustrated in FIGS. 1 through 3, the joint prothesis component system 10 is designed such that the connection surface 24 is a boss 46 having internal or female threads (not shown). The proximal end 34 of the adapter element includes an elongate male member 48 having threads 50 at a proximal end thereof. A distal end of male member 48 extends from a shoulder 52 formed upon the adapter 16 and includes threads 54 formed on the male member 48 adjacent to shoulder 52.

A locking ring 56 preferably is mounted upon male member 48. The locking ring 56 has internal threads 58 that are matable with the threads 54 of the male member. When the proximal end 34 of the adapter element 16 is mounted upon the proximal end 28 of the elongate extension 20, the adapter 16 may be rotated to achieve a desired orientation for the offset of longitudinal axes 42, 44. When the desired orientation is achieved, locking ring 56 may be manipulated until its proximal surface 57 abuts surface 24 of elongate extension 20. This will secure the distal end 36 of the adapter element in the desired orientation with respect to the first end 34 of the adapter element. For example, in the embodiment shown in FIGS. 1 through 3, the longitudinal axis 44 can be rotated about the longitudinal axis 42 over a 360 degree range. The locking ring enables the desired orientation to be maintained once it is achieved.

The stem element 14, illustrated in FIGS. 1 through 3, preferably is of a type that is standard and well known in the endoprothesis art. The stem element 14 is an elongated member having proximal 28 and distal 30 ends. The proximal end 28 includes a connection surface 32 that is matable with the connection surface 40 of adapter element 16. Preferably, the connection surface 32 lies on a longitudinal axis 15 of the stem that extends through the proximal and distal ends of stem 14.

In a preferred embodiment, the connection surface 32 includes an abutment shoulder 66 from which extends, in a proximal direction, a male member 68. Male member 68 preferably includes threads 70 at a proximal end thereof. The threads 70 are intended to threadingly engage female threads (not shown) that are formed within the distal end 36 adapter element 16.

The use of a standard tibial stem that is able to threadingly mate with the distal end of an adapter element is desirable because it enables standard tibial stems to be used with the tray and adapter components of the present invention. Tibial stems are available with varying physical characteristics, including length, diameter and surface features. In essence this invention enables a surgeon to achieve a desired degree of offset, to accommodate virtually any anatomical peculiarity of a patient, while at the same time using a single, standard tibial stem. Although the illustrated tibial stem is intended to threadingly engage the adapter, it is understood that the tibial stem may alternatively be designed to engage the adapter through an interference fit or by mechanical interlock.

FIGS. 4A–4C illustrate adapter elements 16', 16" and 16"' that have varying degrees of lateral offset between longitudinal axes 42 and 44. Because of the variable tibial anatomies encountered among knee arthroplasty patients more or less offset may be required. The lateral offset between axes 42 and 44 can vary depending upon a patient's anatomical requirements, but the offset generally is in the range of about 1 to 6 mm. As shown in FIGS. 4A through 4C, the adapter elements 16', 16" and 16"' have lateral offset of approximately 2 mm, 3 mm and 4 mm, respectively. A knee prosthesis system can include a variety of adapters each having a different degree of lateral offset between axes 42 and 44, enabling a surgeon to utilize the adapter best suited to a given patient.

Adapter elements 16', 16" and 16"', like adapter element 16, include a connection surface 38' that is matable with connector surface 32 of elongate extension 20. In the illustrated embodiments, connection surfaces 38' include threads 50 that engage internal threads within elongate extension 20. Alternatively, connection surfaces 38', 32 may be appropriately tapered to allow an interference fit with elongate extension 20, or they may include external structures (not shown) to enable a mechanical engagement with elongate extension 20.

FIGS. 5 and 6 illustrate another embodiment of the invention in which a mechanical engagement may be made between the adapter element and the tibial tray. As illustrated, tray element 12 having medial and lateral sides 71, 73, includes an elongate extension 72 having a female opening 74 that is substantially ovoid in shape. Although the illustrated elongate extension 72 is elongated in the medial-lateral directions it is also possible to orient this elongate extension 72 such that it is elongated in alignment with the anterior 75 and posterior 77 sides of the tray. A shoulder 60 is formed within opening 74 to facilitate mechanical interlock with adapter element 76.

The adapter element 76 includes a proximal end 78 that is of an ovoid shape corresponding to that of opening 74 and that is adapted to fit within the female opening 74 in an interference fit. Adapter element 76 includes ribs 62 that are designed to engage shoulder 60 to facilitate mechanical interlock between adapter 76 and elongate extension 72. In one embodiment, the ribs are expanded radially by the stem upon connection of the stem to the distal end 80 of the adapter. Such expansion enables the ribs 62 to engage shoulder 60. It is understood that other connection schemes can be used as well. For example, appropriate tapering of the female opening 74 and proximal end 78 of adapter element 76 can effect an interference fit.

The distal end 80 of the adapter element 76 is configured in a substantially circular shape, similar to distal end 36 of adapter element 16 described above with respect to FIGS. 1 through 3. The distal end 80 is, however, configured such that a longitudinal axis 82 extending therethrough is offset from longitudinal axis 84 extending through elongate extension 72. As so configured, the adapter element 76 may be mounted to the tray element 12 such that the axis 82 is offset from axis 84 in either the medial or lateral direction. Alternatively, if the female opening 74 is configured to be an oval that is elongated in the anterior-posterior direction, the axis 82 may be offset from axis 84 in either the anterior or posterior direction.

Figure 7:
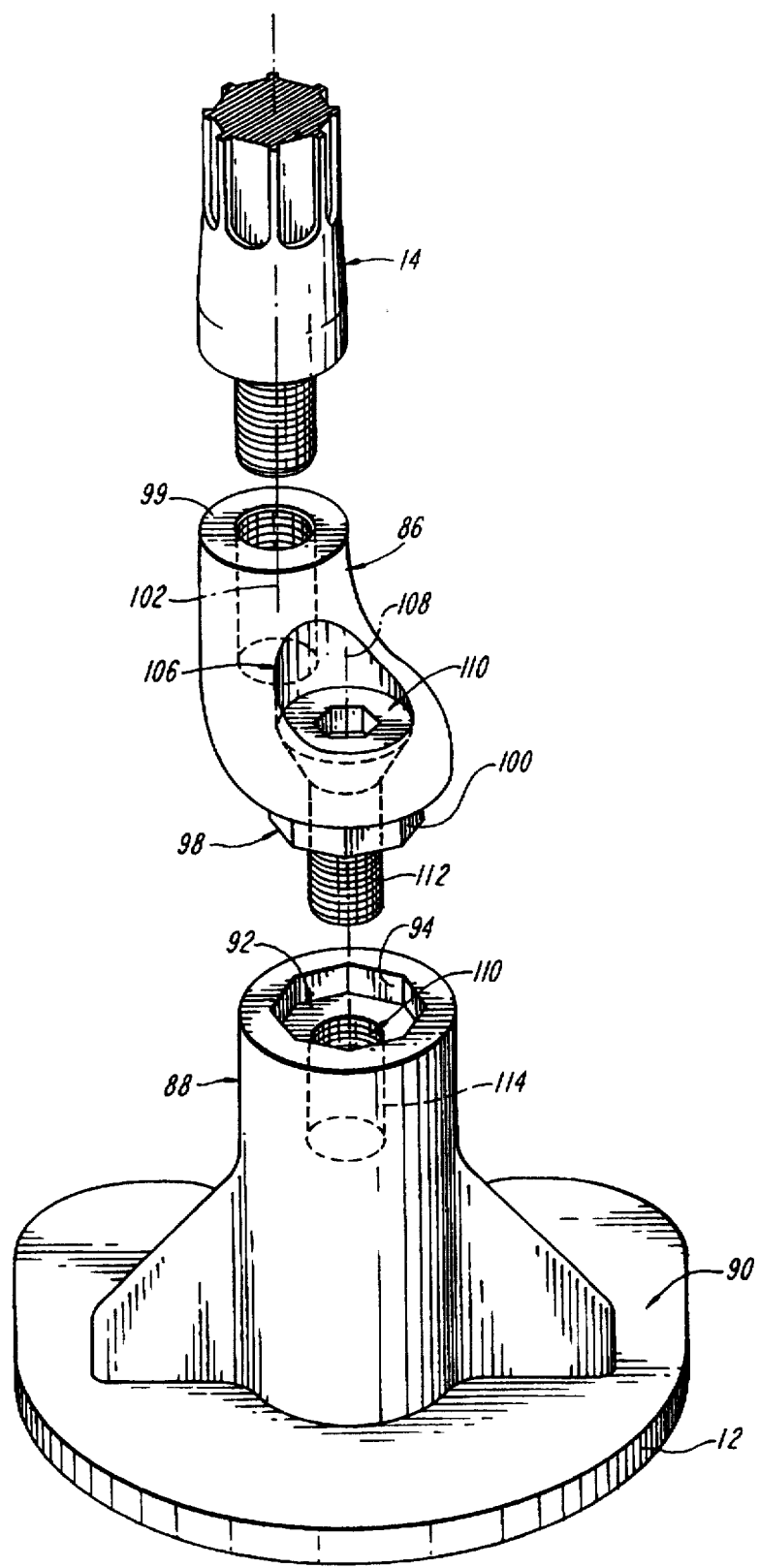
FIG. 7 is an exploded perspective view of another embodiment of a joint prothesis component system according to the present convention, illustrating a tibial tray component, an adapter component, and a portion of a tibial stem.

FIG. 7 illustrates an embodiment of the invention in which adapter element 86 can be joined to the tray element 12 while providing a variety of offset orientation options. As illustrated, an elongate extension 88 mounted on the inferior surface 90 of tray element 12 defines a female cavity 92 of a complex shape. The cavity 92 can be in the shape of a polygon or in a star-shape so as to have a number of discreet rays extending radially from a central point. In the illustrated embodiment, cavity 92 is in the shape of an octagon having eight orientation surfaces 94.

The adapter element 86 has an offset construction in which a longitudinal axis 102 that extends through a distal end 99 thereof is offset from a longitudinal axis 108 that extends through proximal end 98.

The proximal end 98 of adapter element 86 is of a size and shape complementary to that of female cavity 92 such that it is able to be engaged therein. Like cavity 92, proximal end 98 has eight orientation surfaces 100. This construction enables adapter element 86 to be rotated about the longitudinal axis 108 of its proximal end 98 such that any orientation surface 100 thereof can abut any orientation surface 94 of cavity 92, thus yielding eight offset orientation options. One of ordinary skill in the art will readily appreciate that a greater or lesser number of offset options can be achieved by providing a greater or lesser number of orientation surfaces 94, 100 in cavity 92 and proximal end 98.

The distal end 99 of adapter element 86 is configured in a substantially circular shape, similar to distal end 36 of adapter element 16, described above with respect to FIGS. 1 through 3.

As shown in FIG. 7, one way in which the adapter element 86 can be joined to the elongate element 88 of tibial tray 12 is through a threaded connection. The proximal end 98 of adapter 86 may include an aperture 106 which allows access to a bolt 110 that is able to be rotated independent of adapter element 86. The bolt 110 has a threaded end 112 that extends beyond the proximal end 98 of adapter 86 when the bolt is properly seated. The threaded end 112 of bolt 110 engages threads 114 formed in a bolt cavity 116 within elongate extension 88. Alternative connection schemes will be apparent to those having ordinary skill in the art. For example, an interference fit may be achieved between adapter 86 and elongate extensions 98 by appropriate tapering of orientation surfaces 100 and 94.

It is understood that various modifications can be made to the present invention without departing from the intended scope thereof. The entirety of all references noted herein is expressly incorporated by reference herein.

What is claimed is:

1. A modular joint prosthesis component, comprising:

a tray element having a first surface that is mountable upon bone and a second, opposed surface, the first surface including an extension member;

an adapter element having first and second ends wherein a first longitudinal axis extending through the first end is substantially parallel to but offset from a second longitudinal axis extending through the second end, the first end having a connection surface that is selectively matable with the extension member; and an elongate stem mountable within bone, the elongate stem having a first end that is selectively matable with a connection surface on the second end of the adapter element, the stem being mountable upon the adapter element such that a longitudinal axis of the elongate stem is colinear with the longitudinal axis of the second end of the adapter element.

2. The modular joint prosthesis component of claim 1, further comprising a locking element disposed on the adapter element, adjacent to the first surface of the extension member, and being effective to secure the adapter element in a desired orientation when mated with the extension member.

3. The modular joint prosthesis component of claim 1, wherein the tray element is a tibial tray and the elongate stem is a tibial stem.

4. The modular joint prosthesis component of claim 3 wherein the extension member includes a boss member.

5. The modular joint prosthesis component of claim 4 wherein the boss member has internal threads.

6. The modular joint prosthesis component of claim 3 wherein the first end of the adapter element includes a threaded member matable with the boss member.

7. The modular joint prosthesis component of claim 6 wherein the threaded member of the first end of the adapter element is a threaded male member.

8. The modular joint prosthesis component of claim 4 wherein the first end of the adapter element is matable with the extension member in a mechanical engagement.

9. The modular joint prosthesis component of claim 2 wherein the locking element is a locking ring that is threadingly engaged with the adapter element.

10. The modular joint prosthesis component of claim 9 wherein the first end of the adapter element is an elongate male member that extends from a distal end abutting an intermediate shoulder formed on the adapter element to a proximal, threaded end, and wherein the locking element is a female threaded locking ring that engages threads formed on the distal end of the elongate male member, adjacent to the intermediate shoulder.

11. The modular joint prosthesis component of claim 3 wherein the second end of the adapter element is a female threaded member.

12. The modular joint prosthesis component of claim 11 wherein the first end of the elongate stem is a threaded male member which is matable with the female threaded member of the adapter element.

13. The modular joint prosthesis component of claim 1 wherein the first longitudinal axis is colinear with a central longitudinal axis of the tray element.

14. The modular joint prosthesis component of claim 13 wherein the first and second longitudinal axes are offset from each other by approximately 1 to 6 mm.

15. The modular joint prosthesis component of claim 8 wherein the boss member of the extension and the first end of the adapter element each are of an ovoid shape, and wherein the second end of the adapter element is substantially circular in shape and is aligned with one side of the first end of the adapter element, offset from the center of the first end of the adapter element.

16. The modular joint prosthesis of claim 8 wherein the boss member of the extension corresponds to the shape of the first end of the adapter element.

17. The modular joint prosthesis of claim 1 wherein the first end of the adapter element and a boss member on the extension member are of corresponding polygonal shapes, and the second end of the adapter element is of a substantially circular shape and has a longitudinal axis extending therethrough that is offset from the first longitudinal axis such that the adapter element facilitates multiple offset orientations of the extension member of the tray element with respect to the elongate stem.

18. An adapter element, for connection between two components of a joint prosthesis, comprising:

a body having first and second ends wherein a first longitudinal axis extending through the first end is substantially parallel to but offset from a second longitudinal axis extending through the second end;

a first connection surface integral with the first end that is adapted to mate with a first joint prosthesis component; and a second connection surface integral with the second end that is adapted to mate with a second joint prosthesis component;

the adapter element being effective to join the first and second joint prosthesis components together such that a longitudinal axis extending through the second joint prosthesis component is offset from a longitudinal axis extending through the first joint prosthesis component, wherein the first connection surface is of a polygonal shape.

19. An adapter element, for connection between two components of a joint prosthesis, comprising:

a body having first and second ends wherein a first longitudinal axis extending through the first end is substantially parallel to but offset from a second longitudinal axis extending through the second end;

a first connection surface integral with the first end that is adapted to mate with a first joint prosthesis component; and a second connection surface integral with the second end that is adapted to mate with a second joint prosthesis component;

the adapter element being effective to join the first and second joint prosthesis components together such that a longitudinal axis extending through the second joint prosthesis component is offset from a longitudinal axis extending through the first joint prosthesis component, further comprising an aperture extending through the first end thereof and a bolt member having a head and an opposed threaded end, the bolt member being insertable within the aperture to mate the adapter element with the first joint prosthesis component.

* * * * *